United States Patent
O'Neill

(10) Patent No.: US 8,297,330 B2
(45) Date of Patent: Oct. 30, 2012

(54) WELDED KNOT END EFFECTOR

(75) Inventor: David O'Neill, Orange, CT (US)

(73) Assignee: Tyco Healthcare Group LP, Mansfield, MA (US)

(*) Notice: Subject to any disclaimer, the term of this patent is extended or adjusted under 35 U.S.C. 154(b) by 0 days.

(21) Appl. No.: 12/888,652

(22) Filed: Sep. 23, 2010

(65) Prior Publication Data

US 2011/0079341 A1  Apr. 7, 2011

Related U.S. Application Data

(60) Provisional application No. 61/247,702, filed on Oct. 1, 2009.

(51) Int. Cl.
*B32B 37/00* (2006.01)

(52) U.S. Cl. .................... 156/580.2; 156/580.1

(58) Field of Classification Search ............ 156/379.6, 156/379.8, 580, 580.1, 580.2, 581, 583.1, 156/73.1, 73.2
See application file for complete search history.

(56) References Cited

U.S. PATENT DOCUMENTS

| | | | |
|---|---|---|---|
| 3,499,808 A * | 3/1970 | Obeda | 264/249 |
| 3,657,056 A * | 4/1972 | Winston et al. | 156/580.2 |
| 4,669,473 A | 6/1987 | Richards et al. | |
| 4,741,330 A | 5/1988 | Hayhurst | |
| 5,244,520 A * | 9/1993 | Gordon et al. | 156/73.1 |
| 5,464,424 A | 11/1995 | O'Donnell, Jr. | |
| 5,620,555 A * | 4/1997 | Choudhury | 156/580.2 |
| 5,964,765 A | 10/1999 | Fenton, Jr. et al. | |
| 6,596,014 B2 | 7/2003 | Levinson et al. | |
| 6,605,178 B1 * | 8/2003 | Shinohara et al. | 156/379.6 |
| 2003/0149447 A1 | 8/2003 | Morency et al. | |
| 2004/0210226 A1 | 10/2004 | Trieu | |
| 2004/0260343 A1 | 12/2004 | Leclair | |
| 2005/0267531 A1 | 12/2005 | Ruff et al. | |
| 2006/0116718 A1 | 6/2006 | Leiboff | |
| 2008/0208216 A1 | 8/2008 | Cerier | |
| 2009/0192439 A1 | 7/2009 | Lamson et al. | |

* cited by examiner

*Primary Examiner* — James Sells

(57) ABSTRACT

An apparatus for forming an end effector includes a welding device having a welder positioned adjacent to a base, and a die coupled to one end of the welder. The base and the welder are movable relative to each other. The welder, base or die includes a source of heat that is applied to a portion of the suture disposed between the welder and the base.

17 Claims, 6 Drawing Sheets

WELDED KNOT END EFFECTOR

CROSS-REFERENCE TO RELATED APPLICATIONS

The present application claims the benefit of and priority to U.S. Provisional Patent Application Ser. No. 61/247,702, filed Oct. 1, 2009, the disclosure of which is herein incorporated by reference in its entirety.

BACKGROUND

1. Technical Field

The present disclosure relates to sutures for use in medical procedures. More particularly, the present disclosure relates to a welded knot end effector.

2. Background of Related Art

Medical sutures may be formed from a variety of materials and may be configured for use in limitless applications. The proximal end of the suture may have a sharpened tip, or may include a needle, for penetrating tissue. A distal end of the suture may include an anchor or end effector for maintaining the suture in engagement with the tissue as the suture is pulled through the tissue. End effectors are available in many size and configurations.

In many instances, a clinician may prefer to tie a knot in the suture to anchor the suture within the tissue. Although the clinician may find this practice convenient, the knot formed on the end of the tissue is not always suitable to prevent the suture from being pulled through the tissue, for example, the knot slips or is too small to engage the tissue. Additionally, the tying of a knot, especially with the fine suture material required for use in many procedures, is tedious and time consuming.

Therefore, a continuing need exists for an end effector and a method of making an end effector.

SUMMARY

A method of forming a welded end effector is presently disclosed. The method includes providing a length of suture including a knot and a welding device selectively engagable with the knot, the welding device includes a base and a welder. Additionally the method includes positioning a portion of the suture within a welding device, activating the welding device and reducing the gap between the welder and the base to weld the knot. Activating the welding device may include activating contact heating, radiant heating or ultrasonic welding. The gap between the welding device and the base may be from 0.001 inches to 0.05 inches. The knot may include a first section and a second section, each of the first and second sections including a plurality of throws.

Also disclosed is a welding device for forming a welded end effector. The welding device includes a base and a welder positioned adjacent to the base. The welder may include a die extending towards the base. The welder is capable of relative movement with respect to the base. The die may be made of titanium. The base may include grooves to form a raised portion on the welded end effector to enhance engagement of the welded end effector with a tissue. The welding device is configured to retain a distal end of a suture between the die and the base.

Further disclosed is a system for forming an end effector. The system includes a suture and a welding device. The suture may include a body portion defining a longitudinal axis and a knot integrally formed from the body portion. The welding device may include a welding device having a die coupled to one end of the welder and a base supporting at least a portion of the suture and a welder positioned adjacent to the base and movable relative to the base. Relative movement of the welder and the base compresses the knot disposed therebetween.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
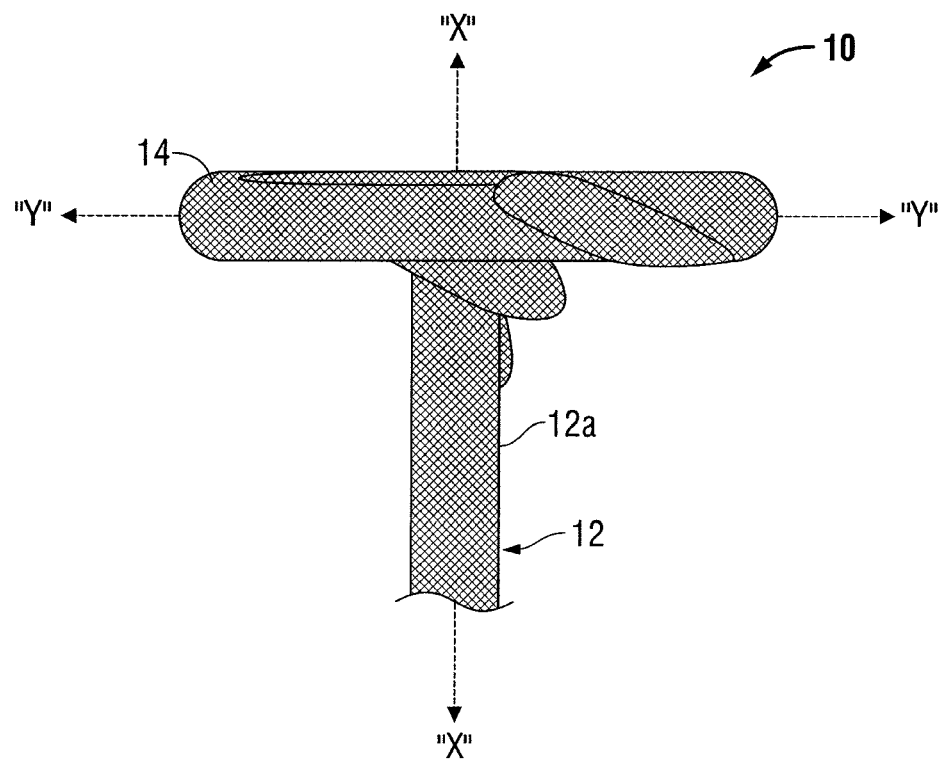
FIG. 1 is a side view of an end effector according to an embodiment of the present disclosure.
Figure 2:
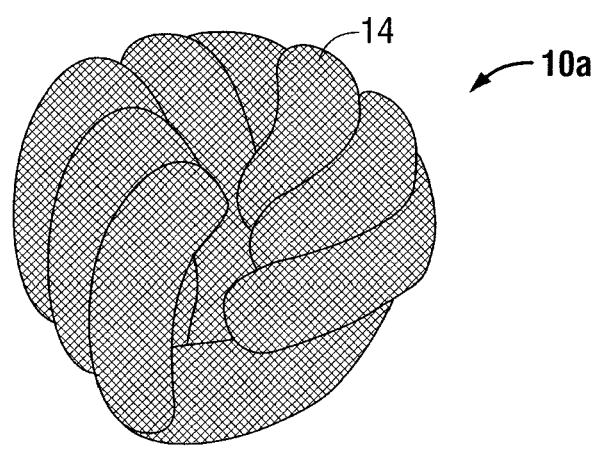
FIG. 2 is a top view of the end effector of FIG. 1.

Referring initially to FIGS. 1 and 2, an embodiment of an end effector according to the present disclosure is shown generally as welded end effector 10. Although, as shown, end effector 10 if formed on a first end 12a of suture 12, end effector 10 may be formed anywhere along the length of suture 12. Suture 12 may be formed of degradable materials, non-degradable materials, and combinations thereof. More particularly, suture 12 may be formed of a degradable material selected from the group consisting of polyesters, polyorthoesters, polymer drugs, polydroxybutyrates, lactones, proteins, cat gut, collagens, carbonates, homopolymers thereof, copolymers thereof, and combinations thereof. In other embodiments, suitable degradable materials which may be utilized to form suture 12 include natural collagenous materials or synthetic resins including those derived from alkylene carbonates such as trimethylene carbonate, tetramethylene carbonate, and the like; caprolactone; dioxanone; glycolic acid; lactic acid; homopolymers thereof; copolymers thereof and combinations thereof. In some embodiments, glycolide and lactide based polyesters, especially copolymers of glycolide and lactide, may be utilized to form suture 12.

Suitable non-degradable materials which may be utilized to form suture 12 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, cotton, linen, carbon fibers, and the like. The polypropylene may be isotactic polypropylene or a mixture of isotactic and syndiotactic or atactic polypropylene.

Suture 12 may be formed using any technique within the purview of those skilled in the art, such as, for example, extrusion, molding and/or solvent casting. In some embodiments, suture 12 may include a yarn made of more than one filament, which may contain multiple filaments of the same or different materials. Where suture 12 is made of multiple filaments, suture 12 may be made using any known technique such as, for example, braiding, weaving or knitting. Suture 12 may also be combined to produce a non-woven suture. Suture 12 may be drawn, oriented, crinkled, twisted, comingled or air entangled to form yarns as part of the suture forming process. In one embodiment, a multifilament suture may be produced by braiding. The braiding may be done by any method within the purview of those skilled in the art.

With reference still to FIGS. 1 and 2, welded end effector 10 is configured to prevent complete reception of suture 12 through tissue or other material. End effector 10 forms a flattened, substantially disk-shaped member 14 on a first portion 12a of suture 12. End effector 10 defines a horizontal axis "y" formed perpendicular to a longitudinal axis "x" of suture 12. As will be discussed in greater detail below, configuration of the disk 14 depends on the size and configuration of end effector 10 prior to welding and on the pressure applied by the welding device 150 shown in FIG. 4.

Figure 3:
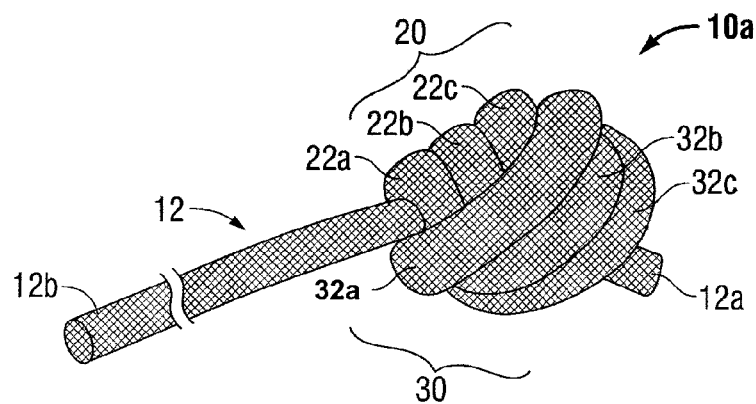
FIG. 3 is a perspective view of the end effector of FIGS. 1 and 2 prior to being welded.

Turning now to FIG. 3, end effector 10 is shown in a pre-welded form. Pre-welded end effector 10a forms a knot several times thicker than suture 12 on distal portion 12a of suture 12. Pre-welded end effector 10a includes first and second sections 20, 30. Each of first and second sections 20, 30 is formed form a plurality of throws 22a-c, 32a-c, respectively. As used herein, a throw is defined as an at least three-hundred and sixty degree (360°) wrapping or weaving of two limbs. As shown, first and second sections 20, 30 each include three throws 22a-c, 32a-c. It is envisioned, however, that first and second sections 20, 30 may include any number of throws 22, 32. It is further envisioned that the number of throws on first section 20 need not be equal to the number of throws on second section 30. A second end 12b of suture 12 may include one or more needles (not shown). Suture 12 may include one or more barbs along the length thereof.

For a more detailed discussion of pre-welded end effector 10a, including methods of making the same, please refer to commonly owned U.S. patent application Ser. No. 12/852,672, filed concurrently herewith, the content of which is incorporated herein by reference in its entirety.

Figure 4:
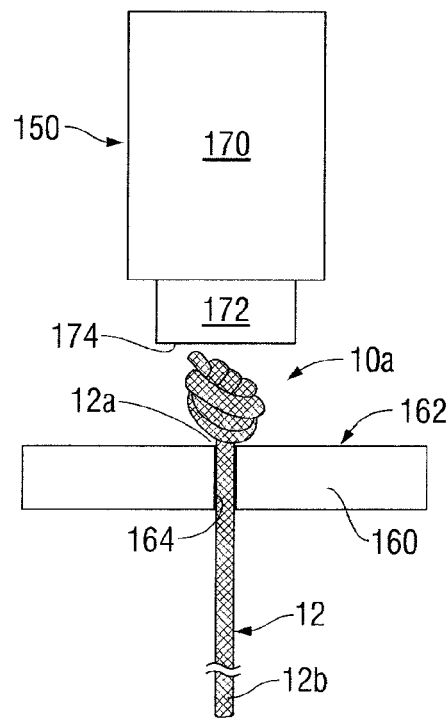
FIG. 4 is a end effector welding device according to an embodiment of the present disclosure.
Figure 5:
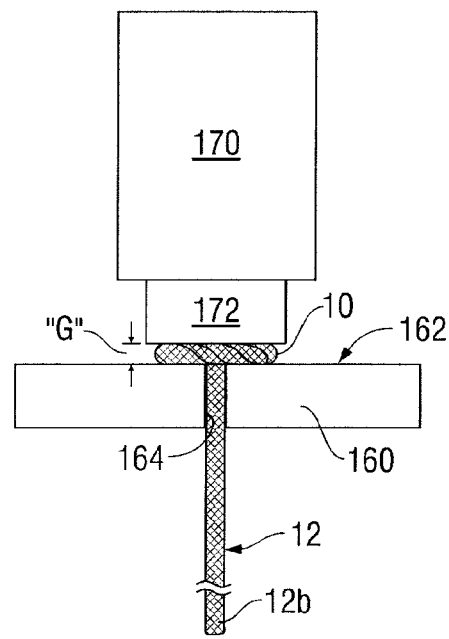
FIG. 5 is the end effector welding device of FIG. 4, during the welding of an end effector.

Turning now to FIGS. 4 and 5, an apparatus for forming welded end effector 10 is shown generally as welding device 150. Although discussed with reference to welding end effector 10, welding device 150 may be modified to weld end effectors of various shapes and sizes. Welding device 150 includes a base or nest 160 for maintaining suture 12 during the forming of end effector 10 and a welder 170 for forming end effector 10. Although throughout the remainder of the discussion reference will be made to welder 170 as being of the ultrasonic variety, it is envisioned that welder 170 may include any device capable of causing pre-formed end effector 10a to become formable (i.e., other energy sources, heat, light, etc.). It is also envisioned that the source of heat or energy may be in the base 160 or the welder 170, or both.

Figure 6:
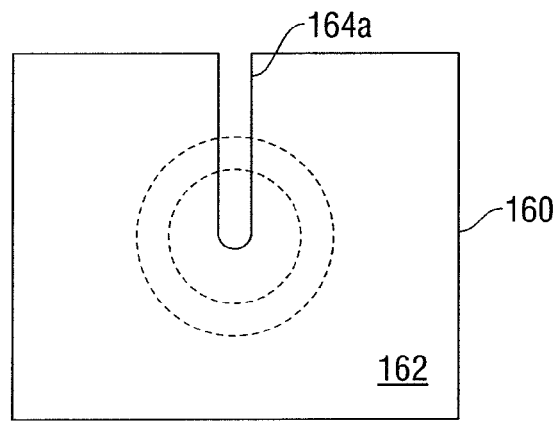
FIG. 6 is a top view of a base for the end effector welding device of FIGS. 4 and 5.
Figure 7:
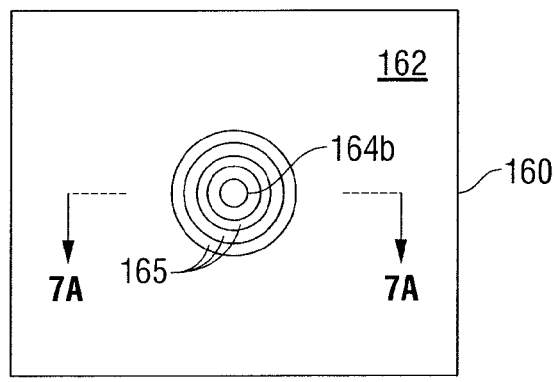
FIG. 7 is a top view of an alternate base of the end effector welding device of FIGS. 4 and 5.
Figure 7A:
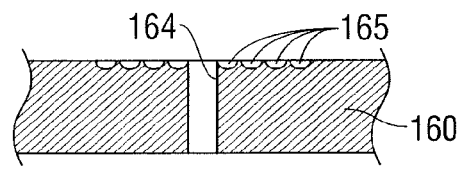
FIG. 7A is a partial cross-sectional side view of the base of FIG. 7 taken along lines 7A-7A of FIG. 7.

With continued reference to FIGS. 4 and 5, base 160 of welding apparatus 150 includes a substantially flat working surface 162 and an opening 164 extending therethrough. Opening 164 may include a slot 164a, as shown in FIG. 6, or may instead including a throughbore 164b, as shown in FIG. 7. Opening 164 is configured to receive a second end 12b of suture 12 therethrough. The size of opening 164 may be varied depending on the size of suture 12. In one embodiment, opening 164 is no greater than two-thousandths of an inch (0.002") larger than the diameter of suture 12.

Figure 8:
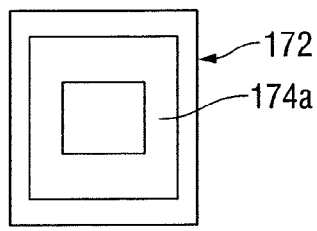
FIG. 8 is a bottom view of a forming die for the end effector welding device of FIGS. 4 and 5.
Figure 8A:
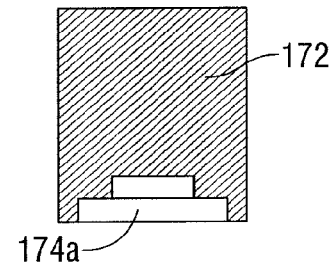
FIG. 8A is a cross-sectional side view of the forming die of FIG. 8.
Figure 9:
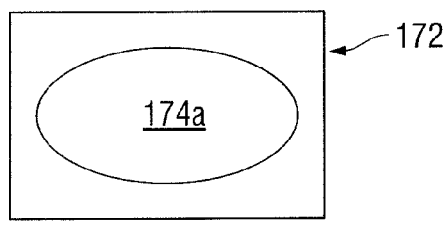
FIG. 9 is a bottom view of a forming die for the end effector welding device of FIGS. 4 and 5.
Figure 9A:
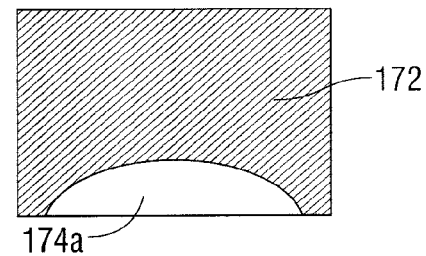
FIG. 9A is a cross-sectional side view of the forming die of FIG. 9.
Figure 10:
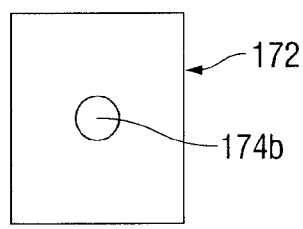
FIG. 10 is a bottom view of a forming die for the end effector welding device of FIGS. 4 and 5.
Figure 10A:
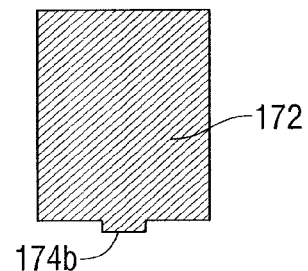
FIG. 10A is a cross-sectional side view of the forming die of FIG. 10.

Still referring to FIGS. 4 and 5, welder 170 includes a die 172 for forming end effector 10. Welder 170 may include a device capable of ultrasonically vibrating die 172. For example, welder 170 may include a Branson 20 KHz ultrasonic welder. Die 172 may be formed of titanium or other suitable material. Die 172 includes a contact surface 174 for engaging end effector 10a. Contact surface 174 may be substantially flat, or instead contact surface 174 may include recess 174a (FIGS. 8A and 9A) and/or raised portion 174b (FIG. 10A). Recess(es) 174a may be rectangular (FIG. 8), circular, oval (FIG. 9) or any other configuration. Recess(es) 174a are configured to form a raised or contoured portion(s) (not shown) in a top surface of end effector 10 during the welding process. Raised surface(s) 174b is configured to form a recess(es) (not shown) in the top surface of end effector 10. The raised surface(s) and/or recess(es) (not shown) formed in the top surface of end effector 10 may be configured to enhance tissue engagement of end effector 10 and/or to facilitate grasping of end effector 10. Welder 170 may weld the end effector 10 by any means designed to soften pre-welded end effector 10a, for example by applying contact heating, radiant heating or ultrasonic. It is envisioned that base 160 of welding apparatus 150 may include an ultrasonic mechanism (not shown) for ultrasonically vibrating base 160 during the forming of end effector 10. In particular, welder 170 includes a source of heat or energy as known in the art. It is envisioned that the source of heat or energy source may be located in the welder, the die, the base, or combinations thereof. The heat source may be an ultrasonic heat source, a radiant heat source, or a contact heat source.

Turning to FIG. 7, in one embodiment, working surface 162 of base 160 includes grooves or indents 165 formed about opening 164. During welding of end effector 10, grooves 165 form raised portions (not shown) in a bottom surface of end effector 10. Alternatively, working surface 162 may include one or more raised surfaces (not shown) for forming one or more recess in the bottom surface of end effector 10 during welding of end effector 10. The ridges and/or recess may be configured to enhance tissue engagement of end effector 10 and/or to facilitate grasping of end effector 10.

With reference again to FIGS. 4 and 5, the operation of welding device 150 will be described. Initially, a pre-welded end effector 10a is formed in first end 12a of suture 12 and any excess material is trimmed away. Pre-welded end effector 10a may be formed on site or instead be provided on suture 12. Second end 12b of suture 12 is then received through opening 164 of base 160 such that pre-welded end effector 10a is received on working surface 162 of base 160 adjacent to ultrasonic welder 170.

When using an ultrasonic heating source, welder 170 is then activated to vibrate die 172. Die 172 is then brought into contact with pre-welded end effector 10a to form end effector 10. In one embodiment, welder 170 is configured to be approximated towards base 160. In another embodiment, base 160 is configured to be approximated towards welder 170. In yet another embodiment, both base 160 and welder 170 are configured to be approximated towards one another. Regardless of whether base 160 and/or welder 170 is approximated, approximation between base 160 and welder 170 occurs until a gap "G" is formed between working surface 162 of base 160 and contact surface 174 of die 172. The distance of gap "G" is dependent on the thickness of suture 12, the size of pre-welded end effector 10a and/or the desired diameter of resulting end effector 10. In one embodiment, gap "G" ranged from one-thousandth of an inch (0.001") to five-hundredths of an inch (0.05").

Still referring to FIGS. 4 and 5, when using an ultrasonic energy source contacting pre-welded end effector 10a with contact surface of vibrating die 172 causes pre-welded end effector 10a to soften or melt. In one embodiment, the welding parameters range from half of a joule (0.5 J) to sixty joules (60 J) and includes a minimum hold time of a quarter of a second (0.25 s). Base 160 and/or welder 170 are moved away from each other and suture 12 including end effector 10 is removed from opening 164 formed in base 160. Welding of pre-welded end effector 10a prevents unraveling of the end effector during use. Welding of pre-welded end effector 10a also increases the surface of end effector 10a that comes into contact with tissue forming disk 14 (FIG. 1), thereby distributing load force more effectively, allowing for a greater load to be exerted before failure of either the tissue or end effector 10.

Figure 11:
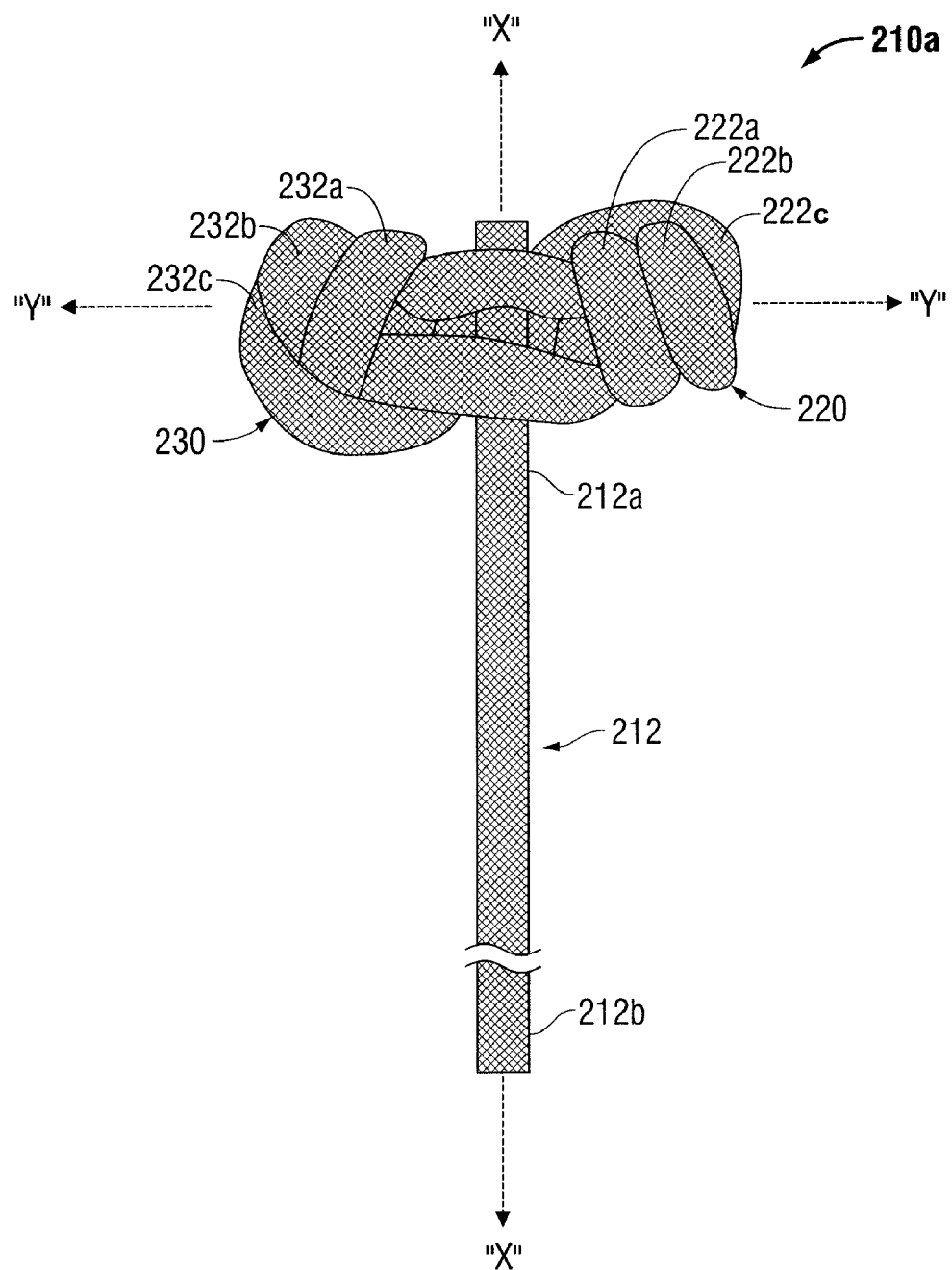
FIG. 11 is an alternate embodiment of an end effector according to the present disclosure, prior to being welded.
Figure 12:
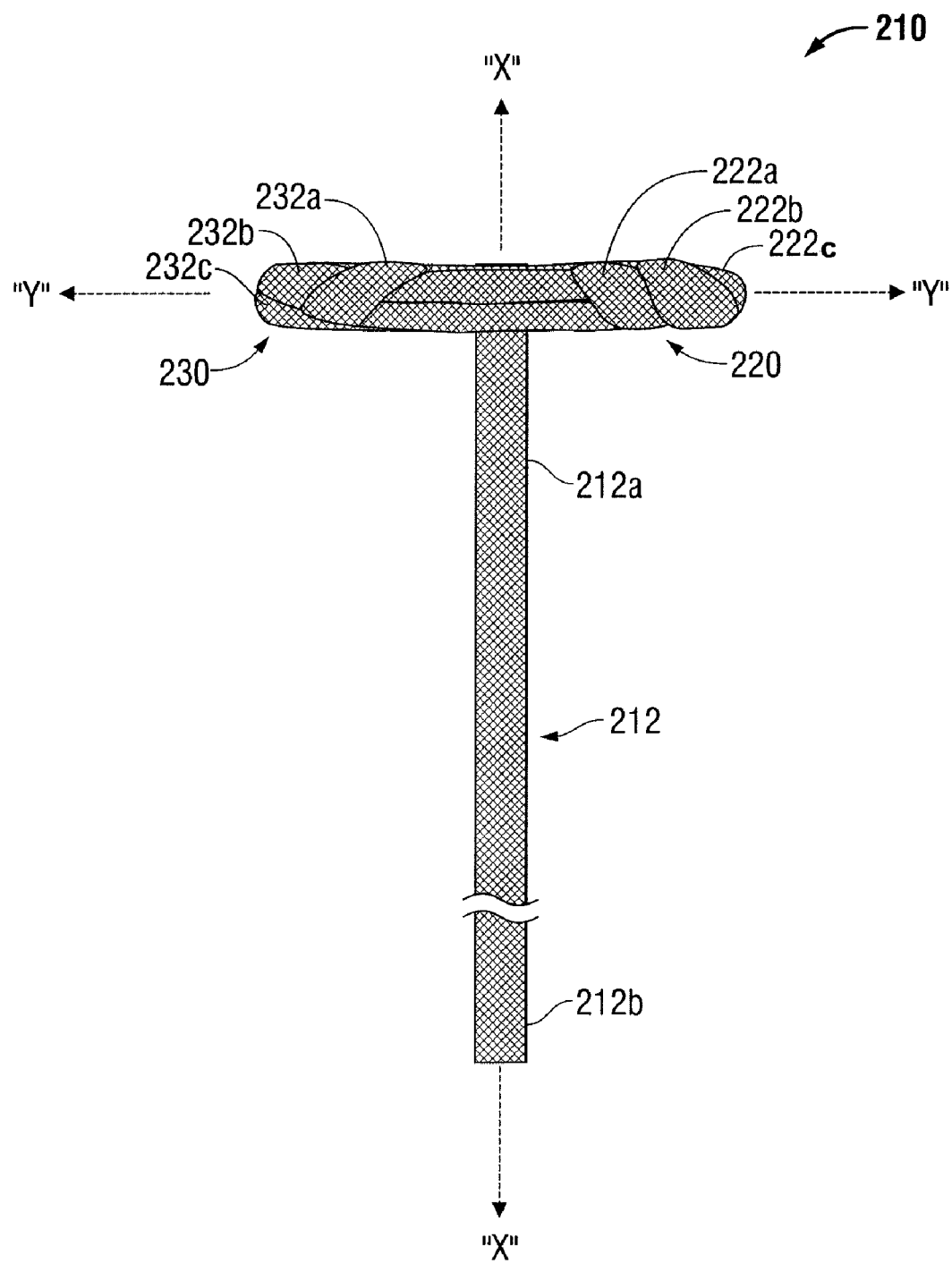
FIG. 12 is a side view of an alternative embodiment of an end effector after welding according to the present disclosure.

With reference to FIG. 11, another embodiment of an end effector capable of use with welding device 150 prior to being welded is shown generally as pre-welded end effector 210a. Pre-welded end effector 210a foil is a substantially T-shaped knot formed on first end 212a of suture 212. Pre-welded end effector 210a defines an axis "Y" extending perpendicular to a longitudinal axis "X" of suture 212. Pre-welded end effector 210a includes first and second extensions 220, 230 extending perpendicularly with respect to axis x from suture 212 in opposite directions along axis "Y" to form a T-shape. Each of first and second extension 220, 230 is formed from a plurality of throws 222a-c, 232a-c, respectively, thereby forming undulated members. As shown, first and second extensions 220, 230 each include three throws 222a-c, 232a-c. It is envisioned, however, that first and second extensions 220, 230 may include any number of throws 222, 232. It is further envisioned that the number of throws on first extension 220 need not be equal to the number of throws on second extension 230. A second end 212b of suture 212 may include one or more needles (not shown) and/or may include one or more barbs. Pre-welded end effector 210a may be welded in the same manner as described above with regards to pre-welded end effector 10a to form end effector 210 (FIG. 12).

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An apparatus for forming a welded end effector, comprising:
 a welding device having a welder positioned adjacent a base, at least one of the base and the welder being movable relative to the other, wherein the base defines an opening therethrough for reception of a suture; and
 a die coupled to one end of the welder,
 wherein relative movement of the welder and the base compresses a knot located on a distal end of the suture disposed therebetween,
 and wherein at least one of the welder, the base and the die includes a energy source.

2. The apparatus of claim 1, wherein the die is made of titanium.

3. The apparatus of claim 1, wherein the suture knot is formed of a degradable material.

4. The apparatus of claim 1, wherein the suture knot is formed of a non-degradable material.

5. The apparatus of claim 1, wherein the base includes grooves to form a raised portion on the welded end effector to enhance engagement of the welded end effector with a tissue.

6. The apparatus of claim 1, wherein the opening in the base defines a slot.

7. The apparatus of claim 6, wherein the slot extends from a lateral edge of the base.

8. The apparatus of claim 5, wherein the grooves are concentric.

9. The apparatus of claim 8, wherein the concentric grooves are formed about the opening in the base.

10. An apparatus for forming an end effector, comprising:
 a welder;
 a base positioned adjacent the welder, wherein at least one of the base and the welder is movable relative to the other, wherein the base defines an opening for receipt of the suture body therethrough; and
 a die coupled to one end of the welder, wherein at least one of the base and the die defines a plurality of concentric grooves.

11. The apparatus of claim 10, wherein relative movement of the welder and the base compress a knot located on a distal end of a suture disposed between the welder and the base to form the end effector.

12. The system of claim 1, wherein the concentric grooves are formed about the opening in the base.

13. The system of claim 12, wherein the opening in the base defines a slot.

14. The apparatus of claim 13, wherein the slot extends from a lateral edge of the base.

15. The apparatus of claim 1, wherein the opening in the base defines a longitudinal axis extending through the die.

16. The apparatus of claim 1, wherein the opening in the base defines a longitudinal axis extending along a path of relative movement of the anvil and the base.

17. The apparatus of claim 10, wherein the base and the die each define a plurality of concentric grooves.

* * * * *